United States Patent [19]

Weibël et al.

[11] 3,932,536

[45] Jan. 13, 1976

[54] PROCESS FOR PREPARING HYDROXYDIPHENYL

[75] Inventors: Oskar Weibël; Hans-Helmut Schwarz, both of Krefeld, Germany

[73] Assignee: Bayer Aktiengesellschaft, Leverkusen, Germany

[22] Filed: Mar. 11, 1974

[21] Appl. No.: 450,251

[30] Foreign Application Priority Data

Mar. 26, 1973 Germany............................ 2314947

[52] U.S. Cl. .............................................. 260/620
[51] Int. Cl.² ........................................ C07C 37/06
[58] Field of Search ............. 260/620; 252/440, 443

[56] References Cited
FOREIGN PATENTS OR APPLICATIONS 2,049,809   4/1972   Germany ............................ 260/620

*Primary Examiner*—Norman Morgenstern
*Attorney, Agent, or Firm*—Burgess, Dinklage & Sprung

[57] ABSTRACT

Hydroxydiphenyl is prepared by dehydrogenating a starting material comprising a completely and/or partly hydrogenated hydroxydiphenyl in the gaseous phase in the presence of a dehydrogenation catalyst. The starting material is free from autoxidation products less volatile than the completely or partially hydrogenated hydroxydiphenyl, or of a peroxidic nature, and only contain products of an acid nature to such an extent than the acid number of the starting material is less than 0.2.

5 Claims, No Drawings

PROCESS FOR PREPARING HYDROXYDIPHENYL

BACKGROUND

This invention relates to a process for the production of hydroxydiphenyl.

Hydroxydiphenyl is known to be obtained by catalytically dehydrogenating completely and/or partially hydrogenated hydroxydiphenyl, in the gaseous phase. The dehydrogenation catalysts used for this purpose contain nickel, chromium, aluminium, copper and alkali oxide or carbonate, and in some cases, silver, and are described, for example, in German Pat. No. 1,108,221 and DOS No. 2,049,809.

In addition to hydroxydiphenyl, a number of secondary products and intermediate products, mainly phenol, diphenyl and cyclohexylphenol and, to some extent, diphenylene oxide, are formed in this dehydrogenation process and have to be removed by special purification processes, for example the process described in DOS No. 2,102,476. However, the reaction product to be purified must satisfy certain qualitative requirements if a purification process of this kind is to be carried out successfully both from the technical and economic points of view. The main requirement is that the reaction product to be purified should have as uniform a qualitative and quantitative composition as possible.

On the other hand, the activity of the dehydrogenation catalyst is known to decrease with time so that the conversion is reduced and the composition of the reaction product is altered accordingly. Although this change in composition can be counteracted by reducing the catalyst load and/or by increasing the reaction temperature, reduction of the catalyst load involves a reduction in throughput and, hence, has an adverse effect upon the dehydrogenation process, whilst increasing the reaction temperature promotes secondary reactions to a greater extent than the main reaction, resulting in a deterioration in the composition of the reaction product.

For this reason, the continuous process has to be interrupted after a certain time in order to regenerate or replace the catalyst. However, this again involves a reduction in the output of the installation in which the process is carried out, quite apart from increased costs.

It has also proved to be advantageous to use a crude dehydrogenation product of largely constant composition for purification. As already mentioned, however, it is not possible to obtain a crude product of this kind by conventional dehydrogenation processes. Although it is possible, by storing and mixing dehydrogenation products of different composition in an intermediate stage, to prepare a product of constant composition for the purification process, this involves more work and additional costs.

In order to obviate the disadvantages attending conventional dehydrogenation processes, there is an urgent need for a dehydrogenation process which gives a dehydrogenation product remaining uniform in its composition over prolonged periods without any appreciable change in the activity and selectivity of the dehydrogenation catalyst which, in addition, should have a long service life.

SUMMARY

We have now found that, in the production of hydroxydiphenyl by the catalytic gaseous phase dehydrogenation of completely and/or partially hydrogenated hydroxydiphenyl, in the presence of dehydrogenation catalysts containing nickel, chromium, aluminium, copper and alkali sulphate and/or alkali carbonate, the service life of these catalysts can be considerably lengthened and the aforementioned disadvantages of conventional processes can be obviated by using a starting material which is free from autoxidation products less volatile than the completely or partially hydrogenated hydroxydiphenyl present in the starting material, or those of a peroxidic nature, and which only contains products of an acidic nature to the extent that the acid number of the starting material is less than 0.2, and preferably less than 0.1.

DESCRIPTION

It has been found that the normal, gradual loss of activity from the dehydrogenation catalyst, despite the relatively high reaction temperatures applied of from 300° to 400°C, is attributable less to simple heat damage than to relatively small quantities of secondary products in the starting material used which can be formed even by the relatively brief action of oxygen-containing gases on the starting product, even at room temperature. These catalyst-damaging oxidation products are not known in any detail. Some of the oxidation products are peroxidic and acid in nature. Their presence can be detected by the analytical methods known per se for detecting peroxides and acids.

The secondary products formed by autoxidation from the starting material are largely less volatile than the main material, namely the completely and/or partially hydrogenated hydroxydiphenyl, and for this reason are mostly left behind in the distillation residue where the starting materials of the kind in question are subjected to careful distillation.

Accordingly, the starting material used in accordance with the invention can with advantage be obtained by distilling the conventional starting material to be used in the absence of air and other oxygen-containung gases and protecting it from the action of gases containing oxygen until it is used.

The starting material can also be purified by other methods; for example by treatment with acid-binding, peroxide-binding or -reducing agents.

An effect of using a starting material substantially free from autoxidation products in accordance with the invention, in addition to slowing down deactivation of the dehydrogenation catalyst, is that the relatively small reduction in the activity of the catalyst affects the main reaction and secondary reaction to the same extent so that it can be compensated by increasing the temperature without any appreciable change in the ratio of main and secondary products.

Suitable starting materials for use in the process according to the invention for the production of hydroxydiphenyl are known, the following being mentioned by way of example:

2-cyclohexylidene cyclohexanone,
2-cyclohexenyl cyclohexanone,
2-cyclohexyl cyclohexanone,
2-cyclohexyl cyclohexanol,
2-cyclohexylphenol,
3-cyclohexylphenol,
4-cyclohexylphenol,
2-phenylcyclohexanone,
2-phenylcyclohexanol.

These compounds are easy to prepare. Thus, 2-cyclohexylidene cyclohexanone and 2-cyclohexenyl cyclohexanone, for example, are obtained by condensing cyclohexanone in the presence of acid or basic catalysts by known methods. In addition, these two compounds are formed alongside 2-cyclohexyl cyclohexanone, 2-cyclohexyl cyclohexanol etc as secondary products in the catalytic dehydrogenation of cyclohexanol. They can readily be separated off from the dehydrogenation mixture by distillation and can be used in admixture for the production of 2-hydroxydiphenyl.

Cyclohexylphenol can be obtained by known methods, including the catalytic alkylation of phenol. In addition, 2-cyclohexylphenol is formed as a secondary product alongside 2-phenyl cyclohexanone and 2-phenyl cyclohexanol, 2-cyclohexyl cyclohexanol and 2-cyclohexyl cyclohexanone, in the synthesis of 2-hydroxydiphenyl.

Catalysts suitable for use in the process according to the invention are known per se and are described, for example, in DOS No. 2,049,809 and DOS No. 2,146,052.

In general, the process according to the invention is carried out by passing the starting material, which is free from autoxidation products, especially those less volatile than the completely or partially hydrogenated hydroxydiphenyl present in the starting material, and those of a peroxidic nature, and which only contains autoxidation products of an acid nature to the extent that the acid number of the starting material is less than 0.2, preferably less than 0.1, in the vapour phase over the catalyst at a temperature of from 300° to 400°C, more particularly at a temperature of from 320 to 350°C, under normal or reduced pressure. The apparatus in which the reaction is carried out is known per se.

In addition to hydroxydiphenyl, the reaction product comprises intermediate compounds, especially cyclohexyl phenol, most of which can be reused as a starting material. In the production of 2-hydroxydiphenyl, the reaction product has the appropriate composition for purification by the process described in DOS No. 2,102,476.

The process according to the invention has the following advantages over the prior art:

The service life of the catalyst is considerably increased, the reaction product having substantially the same composition over most of the service life of the catalyst. As already described, this is of crucial importance so far as further purification is concerned. In addition, there is no longer any need for the otherwise necessary (DOS No. 2,049,809) frequent regeneration of the catalyst which interrupts the continuous process and interferes considerably with production.

O-Hydroxydiphenyl is a known preservative for citrus fruits and is also used in a known manner as a carrier for dyeing with dispersion dyes.

The percentages quoted in the following Examples relate to weight unless otherwise stated.

EXAMPLES

A catalyst prepared as follows in accordance with DOS No. 2,049,809 was used in the following Examples:

8580 g of a catalyst starting material containing 42.7% by weight of nickel, 9.5% by weight of chromium, 3.2% by weight of aluminium and 0.2% by weight of copper, obtained as known per se by precipitating a carbonate-hydroxide mixture containing the elements nickel, aluminium and copper from an aqueous solution consisting of the corresponding nitrates and sulphates (50% : 50%) with sodium carbonate solution, and subsequently reacting the precipitate, after it had been washed, with ammonium bichromate solution, are made into a paste in a solution of 225 g of potassium sulphate in 7900 ml of water. The resulting catalyst paste is dried at 120°C, ground, mixed with 3% of graphite and the resulting mixture is processed in a tabletting press into tablets 5 mm thick.

1000 g of the tablets thus obtained are treated for 2.5 hours at 390°C with 100 liters of hydrogen per hour, and then for 6 hours at around 20 to 40°C with 100 liters/hour of a mixture of 2% by volume of air and 98% by volume of $CO_2$.

The tablets are then ground up and mixed with 2% of graphite, and the resulting mixture is re-tabletted, reduced for 2.5 hours at 390°C with 730 liters of hydrogen per hour and subsequently tempered in a $CO_2$-atmosphere for 30 hours at 100°C:

Powder density:     1.16 g/ml
Specific surface:   136 m²/g
Ni (metallic):      25.6%, Ni (total) 56.2%

In all the Examples, the process was carried out as described below:

Using a vertically arranged tube reactor approximately 550 mm long with a tube diameter of 17 mm, which is filled with 30 ml of the catalyst prepared as described above and the upper part of which serves as evaporation zone, 6.0 g/h of a mixture of 2-cyclohexenyl cyclohexanone and 2-cyclohexylidene cyclohexanone, hereinafter referred to as dianone, obtained by condensing cyclohexanone in the presence of an ion-exchanger resin containing sulphonic acid groups, followed by distillation (cf. Chem. Abstr. 75,5344 y (1971), are introduced at 330°C at the upper end of the reactor and the reaction product is run off from the lower end of the reactor.

EXAMPLE 1

A dianone, during the production, storage and use of which oxygen and/or oxygen-containing gases (for example air) had been carefully kept away by an inert gas atmosphere, and which had an acid number of less than 0.1, was used.

After a start up period of a few hours, the reaction product contains:
  81% of 2-hydroxydiphenyl,
  8% of 2-cyclohexylphenol and 2-phenyl cyclohexanone,
  1% of 2-cyclohexylcyclohexanone and dianone,
  5% of diphenylene oxide, and
  3% of diphenyl.

After 1000 hours' operation, the reaction product contains:
  70 % of 2-hydroxydiphenyl,
  18 % of 2-cyclohexylphenol and 2-phenyl cyclohexanone,
  2 % of 2-cyclohexyl cyclohexanone and dianone,
  4 % of diphenylene oxide, and
  2.5% of diphenyl.

After a total of 4300 hours' operation, the reaction product contains:
  69 % of 2-hydroxydiphenyl,
  18 % of 2-cyclohexylphenol and 2-phenyl cyclohexanone, 4 % of 2-cyclohexyl cyclohexanone and dianone,
4 % of diphenylene oxide, and
2.5% of diphenyl.

During further operation, the reaction temperature is successively increased to the extent required to obtain a reaction product having a 2-hydroxydiphenyl content of around 70%. In this way, a reaction product containing:

70 % of 2-hydroxydiphenyl,
14 % of 2-cyclohexyl phenol and 2-phenyl cyclohexanone,
6 % of 2-cyclohexyl cyclohexanone and dianone,
5.5% of diphenylene oxide, and 2 % of diphenyl, is obtained after a total of 10,000 hours' operation at a final reaction temperature of 350°C.

A dianone, during the production, storage and use of which oxygen and/or oxygen-containing gases had not been kept away, and which had an acid number of greater than 0.2, was used in each of the following comparison Examples.

EXAMPLE 2 (comparison Example)

The dianone used had an acid number of 0.3. Although after production it had been stored in a closed vessel, no effort was made thereafter to keep away oxygen and/or oxygen-containing gases.

After a start-up period of a few hours, the reaction product has the following composition:
81% of 2-hydroxydiphenyl,
7% of 2-cyclohexylphenol and 2-phenyl cyclohexanone,
2% of 2-cyclohexyl cyclohexanone and dianone,
4% of diphenylene oxide,
3% of diphenyl, and
3% of other products.

After approximately 1000 hours' operation, the reaction product contains:
65 % of 2-hydroxydiphenyl,
22 % of 2-cyclohexylphenol and 2-phenyl cyclohexanone,
5 % of 2-cyclohexyl cyclohexanone and dianone,
3.5% of diphenylene oxide, and
2.5% of diphenyl.

After a further 800 hours', the reaction product contains:
60 % of 2-hydroxydiphenyl,
24 % of 2-cyclohexylphenol and 2-phenyl cyclohexanone,
8 % of 2-cyclohexylcyclohexanone and dianone,
3.5% of diphenylene oxide, and
2 % of diphenyl.

EXAMPLE 3 (Comparison Example)

The dianone used had an acid number of 0.5. In order quickly to obtain this state of autoxidation, the dianone used in Example 2 was additionally stirred for 8 hours at room temperature in the presence of air.

After a start-up period of a few hours, the reaction product contains:
77% of 2-hydroxydiphenyl,
7% of 2-cyclohexylphenol and 2-phenyl cyclohexanone,
6% of 2-cyclohexyl cyclohexanone and dianone,
6% of diphenylene oxide, and
2% of diphenyl.

By contrast, after 500 hours, the reaction product contains:
58 % of 2-hydroxydiphenyl,
23 % of 2-cyclohexylphenol and 2-phenyl cyclohexanone,
8 % of 2-cyclohexyl cyclohexanone and dianone,
4.5% of diphenylene oxide, and
2 % of diphenyl.

EXAMPLE 4 (comparison Example)

The dianone used had an acid number of 5.7. In order quickly to obtain this state of autoxidation, the dianone used in Example 2 was additionally stirred for 8 hours at 50°C in the presence of air.

A reaction product, the 2-hydroxydiphenyl content of which drops from 69% to 49% over a period of 200 hours, is obtained.

What is claimed is:

1. In the process for the production of hydroxydiphenyl which comprises dehydrogenating a starting material containing hydrogenated hydroxydiphenyls in the gaseous phase in the presence of a dehydrogenation catalyst comprising nickel, chromium, aluminum, copper and alkali metal sulfate and/or alkali metal carbonate, the improvement which comprises purifying said starting material prior to dehydrogenating so as to be free of autoxidation products less volatile than the hydrogenated hydroxydiphenyls, free of peroxide compounds, and containing only acid products to such an extent that the acid number of the starting material is less than 0.2.

2. Process of claim 1 wherein the starting material is purified prior to dehydrogenation by distillation in the absence of air and other oxygen-containing gases, said purified starting material being protected from oxygen-containing gases until used in the process.

3. Process of claim 1 wherein the starting material has an acid number of less than 0.1.

4. Process of claim 1 wherein the starting material comprises 2-cyclohexylidene cyclohexanone, 2-cyclohexenyl cyclohexanone, 2-cyclohexyl cyclohexanone, 2-cyclohexyl cyclohexanol, 2-cyclohexylphenol, 3-cyclohexylphenol, 4-cyclohexylphenol, 2-phenylcyclohexanone or 2-phenylcyclohexanol, alone or in admixture.

5. Process of claim 1 wherein the dehydrogenation is carried out at a temperature of from 300° to 400°C.

* * * * *